United States Patent
Barrett et al.

(10) Patent No.: US 12,384,764 B2
(45) Date of Patent: Aug. 12, 2025

(54) PHARMACEUTICAL COMPOUNDS

(71) Applicant: Pfizer Inc., New York, NY (US)

(72) Inventors: Matthew Barrett, Stevenage (GB); George Stuart Cockerill, Stevenage (GB); James Good, Stevenage (GB)

(73) Assignee: Pfizer Inc., New York, NY (US)

( * ) Notice: Subject to any disclaimer, the term of this patent is extended or adjusted under 35 U.S.C. 154(b) by 707 days.

(21) Appl. No.: 17/773,136

(22) PCT Filed: Nov. 2, 2020

(86) PCT No.: PCT/GB2020/052769
§ 371 (c)(1),
(2) Date: Apr. 29, 2022

(87) PCT Pub. No.: WO2021/084280
PCT Pub. Date: May 6, 2021

(65) Prior Publication Data
US 2022/0380349 A1    Dec. 1, 2022

(30) Foreign Application Priority Data
Nov. 1, 2019 (GB) ...................... 1915932

(51) Int. Cl.
*C07D 403/12* (2006.01)
*C07D 403/14* (2006.01)

(52) U.S. Cl.
CPC ......... *C07D 403/12* (2013.01); *C07D 403/14* (2013.01)

(58) Field of Classification Search
CPC ............................ C07D 403/12; C07D 403/14
USPC ....................................................... 514/218
See application file for complete search history.

(56) References Cited

U.S. PATENT DOCUMENTS

| | | | |
|---|---|---|---|
| 7,417,152 B2 | 8/2008 | Tung et al. | |
| 2017/0022221 A1 | 1/2017 | Shook et al. | |

FOREIGN PATENT DOCUMENTS

| | | |
|---|---|---|
| WO | 2004026843 A1 | 4/2004 |
| WO | 2004106310 A1 | 12/2004 |
| WO | 2005089769 A1 | 9/2005 |
| WO | 2005089770 A1 | 9/2005 |
| WO | 2005089771 A1 | 9/2005 |
| WO | 2005090319 A1 | 9/2005 |
| WO | 2006113140 A2 | 10/2006 |
| WO | 2011027156 A1 | 3/2011 |
| WO | 2011151651 A1 | 12/2011 |
| WO | 2011151652 A1 | 12/2011 |
| WO | 2016166546 A1 | 10/2016 |
| WO | 2018033714 A1 | 2/2018 |
| WO | 2018085378 A1 | 5/2018 |
| WO | 2018129287 A1 | 7/2018 |
| WO | 2018152413 A1 | 8/2018 |
| WO | 2018226801 A1 | 12/2018 |
| WO | 2019094920 A1 | 5/2019 |
| WO | 2020190935 A1 | 9/2020 |
| WO | 2021032992 A1 | 2/2021 |
| WO | 2021079121 A1 | 4/2021 |
| WO | 2022008911 A1 | 1/2022 |
| WO | 2022008912 A1 | 1/2022 |

OTHER PUBLICATIONS

Chapman et al., RSV604, A Novel Inhibitor of Respiratory Syncytial Virus Replication, Antimicrobial Agents and Chemotherapy, 2007, 51(9):3346-3353.

*Primary Examiner* — Kristin A Vajda
(74) *Attorney, Agent, or Firm* — John A. Wichtowski

(57) ABSTRACT

Benzodiazepine derivatives of formula (I): (I) wherein: each of $R^1$ and $R^2$ is independently H or halo; $R^3$ is H, $C_1$-$C_6$ alkyl or —$NHR^8$; either (i), a, c and e are all bonds, with, b, d and f absent; or b, d, and f are all bonds, with a, c, and e absent; $R^4$ is H or a group selected from $C_1$-$C_6$ alkyl, $C_3$-$C_6$ cycloalkyl and 4- to 10-membered heterocyclyl, the group being unsubstituted or substituted; $R^5$ is H or halo; $R^6$ is —$OR^8$, —$NR^8R^9$ or —$R^8$; $R^7$ is H or halo; each of $R^8$ and $R^9$ is independently H or a group selected from $C^1$-$C^6$ alkyl, $C^3$-$C^6$ cycloalkyl and 4- to 10-membered heterocyclyl, the group being unsubstituted or substituted; n is 1 or 2; and one of V, W and X is N or CH and the other two are CH; and the pharmaceutically acceptable salts thereof are inhibitors of RSV and can therefore be used to treat or prevent an RSV infection.

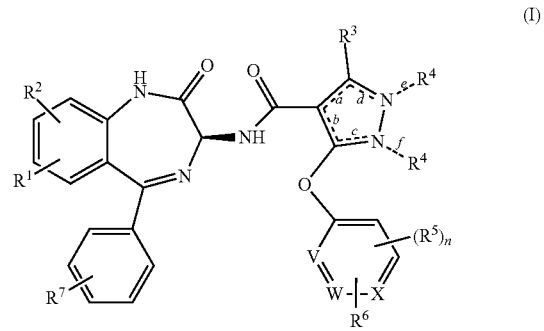

16 Claims, No Drawings

PHARMACEUTICAL COMPOUNDS

CROSS-REFERENCE TO RELATED APPLICATIONS

This application is the U.S. National Stage of PCT/GB2020/052769, with international filing date of Nov. 2, 2020, and which claims priority to GB 1915932.6 filed Nov. 1, 2019, each of which is hereby incorporated by reference in its entirety.

FIELD OF THE INVENTION

The present invention relates to benzodiazepine derivatives and to their use in treating or preventing a respiratory syncytial virus (RSV) infection.

BACKGROUND TO THE INVENTION

RSV is a negative-sense, single-stranded RNA virus of the Paramyxoviridae family. RSV is readily transmitted by secretions from an infected person via surfaces or hand-to-hand transfer. Unlike influenza, it is not transmitted by small-particle aerosols. Following successful inoculation, the incubation period is between four and six days during which time the virus spreads from the nasopharynx to the lower respiratory tract by fusion of infected with uninfected cells and by sloughing of the necrotic epithelium. In infants, coupled with increased mucus secretion and oedema, this can lead to mucus plugging causing hyper-inflation and collapse of distal lung tissue indicative of bronchiolitis. Hypoxia is common and the ability to feed is often impaired because of respiratory distress. In RSV pneumonia, inflammatory infiltration of the airways consists of mononuclear cells and is more generalised, with involvement of the bronchioles, bronchi and alveoli. The duration and degree of viral shedding has been found to correlate with the clinical signs and severity of disease.

RSV is the leading cause of serious respiratory tract infections in infants and young children throughout the world. The highest morbidity and mortality occurs in those born prematurely and for those with chronic lung or heart disease, although many infants hospitalised for RSV infection are otherwise healthy. Severe RSV infection in infancy can lead to several years of recurrent wheezing and is linked to the later development of asthma.

RSV is also a major cause of morbidity and mortality in the elderly and in immunocompromised children and adults as well as those with chronic obstructive pulmonary disease (COPD) and congestive heart failure (CHF).

RSV has a seasonal incidence; it is highly predictable and occurs in the winters of both hemispheres, from September to May in Europe and North America, peaking in December and January, and can occur throughout the year in tropical countries. It affects >90% of infants and young children by the age of two years and as natural immunity is short-lived; many will be re-infected each year. As with influenza, in elderly people, RSV causes around 10% of winter hospitalisations with an associated mortality of 10%.

Current anti-RSV treatment involves the use of a monoclonal antibody to RSV, called palivizumab. Such use of palivizumab is a prophylactic, rather than therapeutic, treatment of RSV. Although this antibody is often effective, its use is restricted to preterm infants and infants at high risk. Indeed, its limited utility means that it is unavailable for many people in need of anti-RSV treatment. There is therefore an urgent need for effective alternatives to existing anti-RSV treatment.

Small molecules have also been proposed as inhibitors of RSV. These include benzimidazoles and benzodiazepines. For instance, the discovery and initial development of RSV604, a benzodiazepine compound having sub-micromolar anti-RSV activity, is described in Antimicrobial Agents and Chemotherapy, September 2007, 3346-3353 (Chapman et al). Benzodiazepine inhibitors of RSV are also disclosed in publications including WO2004/026843 and WO2005/089770 (Arrow Therapeutics Limited); WO2016/166546 and WO2018/033714 (Durham University); and WO2017/015449, WO2018/129287 and WO2018/226801 (Enanta Pharmaceuticals, Inc.).

There exists a need to identify further compounds that have anti-RSV activity, in particular compounds having a combination of potent anti-viral activity and favourable pharmacokinetic properties.

SUMMARY OF THE INVENTION

It has now been found that a novel series of benzodiazepine derivatives have potent anti-RSV activity with favourable pharmacokinetics and good physicochemical properties. Accordingly, the present invention provides a compound which is a benzodiazepinyl pyrazole of formula (I):

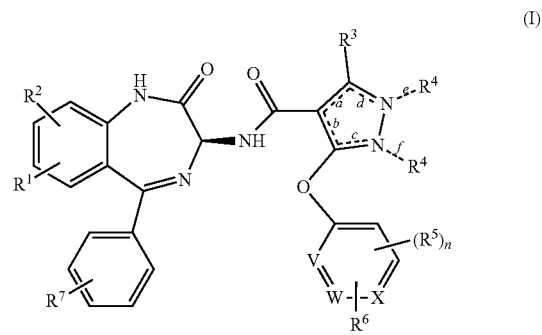

wherein:
each of $R^1$ and $R^2$ is independently H or halo;
$R^3$ is H, $C_1$-$C_6$ alkyl or —$NHR^8$;
either (i) ---a---, ---c--- and ---e--- are all bonds, with ---b---, ---d--- and ---f--- absent; or
---b---, ---d--- and ---f--- are all bonds, with ---a---, ---c--- and ---e--- absent;
$R^4$ is H or a group selected from $C_1$-$C_6$ alkyl, $C_3$-$C_6$ cycloalkyl and 4- to 10-membered heterocyclyl, the group being unsubstituted or substituted;
$R^5$ is halo;
$R^6$ is H, —$OR^8$, —$NR^8R^9$ or —$R^8$;
$R^7$ is H or halo;
each of $R^8$ and $R^9$ is independently H or a group selected from $C_1$-$C_6$ alkyl, $C_3$-$C_6$ cycloalkyl and 4- to 10-membered heterocyclyl, the group being unsubstituted or substituted;
n is 1, 2 or 3;
one of V, W and X is N or CH and the other two are CH;
or a pharmaceutically acceptable salt thereof.

DETAILED DESCRIPTION OF THE INVENTION

When any group, ring, substituent or moiety defined herein is substituted, it is typically substituted by Q as defined below.

A $C_{1-6}$ alkyl group or moiety is linear or branched. A $C_{1-6}$ alkyl group is typically a $C_{1-4}$ alkyl group, or a $C_{4-6}$ alkyl group. Examples of $C_{1-6}$ alkyl groups and moieties include methyl, ethyl, n-propyl, i-propyl, n-butyl, i-butyl, t-butyl, n-pentyl, i-pentyl (i.e. 3-methylbut-1-yl), t-pentyl (i.e. 2-methylbut-2-yl), neopentyl (i.e. 2,2-dimethylpropan-1-yl), n-hexyl, i-hexyl (i.e. 4-methylpentan-1-yl), t-hexyl (i.e. 3-methylpentan-3-yl) and neopentyl (i.e. 3,3-dimethylbutan-1-yl). For the avoidance of doubt, where two alkyl moieties are present in a group, the alkyl moieties may be the same or different. A $C_{1-6}$ alkyl group is unsubstituted or substituted, typically by one or more groups Q as defined below. For example, a $C_{1-6}$ alkyl group is unsubstituted or substituted by 1, 2 or 3 groups Q as defined below.

Q is halo, nitro, —CN, OH, $C_{1-6}$ alkoxy, $C_{1-6}$ hydroxyalkyl, $C_{1-6}$ alkylthio, $C_{1-6}$ alkyl, $C_{1-6}$ haloalkyl, $C_{1-4}$ haloalkoxy, —$CO_2R'$, —$NR'_2$, —$SR'$, —$S(=O)R'$, —$S(=O)_2R'$, $C_3$-$C_{10}$ cycloalkyl, 5 to 10-membered heterocyclyl, 5- to 12-membered aryl or 5- to 10-membered heteroaryl, wherein each R' is independently selected from H, $C_{1-6}$ alkyl, $C_{3-10}$ cycloalkyl, 5 to 10-membered heterocyclyl, $C_6$-$C_{10}$ aryl and 5- to 10-membered heteroaryl. For the avoidance of doubt, the alkyl, alkoxy, alkylthio, cycloalkyl, heterocyclyl, aryl and heteroaryl moieties in these definitions are themselves typically unsubstituted.

A $C_{1-6}$ alkoxy group is linear or branched. It is typically a $C_{1-4}$ alkoxy group, for example a methoxy, ethoxy, propoxy, i-propoxy, n-propoxy, n-butoxy, sec-butoxy or tert-butoxy group. A $C_{1-6}$ alkoxy group is unsubstituted or substituted, typically by one or more groups Q as defined above.

A $C_{1-6}$ alkylthio group is linear or branched. It is typically a $C_{1-4}$ alkylthio group, for example a methylthio, ethylthio, propylthio, i-propylthio, n-propylthio, n-butylthio, sec-butylthio or tert-butylthio group. A $C_{1-6}$ alkylthio group is unsubstituted or substituted, typically by one or more groups Q as defined above.

A halogen or halo group is F, Cl, Br or I. Typically it is F or Cl. A $C_{1-6}$ alkyl group substituted by halogen may be denoted "$C_{1-6}$ haloalkyl", which means a $C_{1-6}$ alkyl group as defined above in which one or more hydrogens is replaced by halo. Likewise a $C_{1-6}$ alkoxy group substituted by halogen may be denoted "$C_{1-6}$ haloalkoxy", which means a $C_{1-6}$ alkoxy group as defined above in which one or more hydrogens is replaced by halo. Typically, $C_{1-6}$ haloalkyl or $C_{1-6}$ haloalkoxy is substituted by 1, 2 or 3 said halogen atoms. Haloalkyl and haloalkoxy groups include perhaloalkyl and perhaloalkoxy groups such as —$CX_3$ and —$OCX_3$ wherein X is a halogen, for example —$CF_3$—$CCl_3$—$OCF_3$ and —$OCCl_3$.

A $C_{1-6}$ hydroxyalkyl group is a $C_{1-6}$ alkyl group as defined above, substituted by one or more OH groups. Typically, it is substituted by one, two or three OH groups. Preferably, it is substituted by a single OH group.

A $C_6$-$C_{10}$ aryl group is an aromatic carbocyclic group containing from 6 to 10 carbon atoms. It is monocyclic or a fused bicyclic ring system in which an aromatic ring is fused to another aromatic carbocyclic ring. Examples of a $C_6$-$C_{10}$ aryl group include phenyl and naphthyl. When substituted, an aryl group is typically substituted by a group Q as defined above, for instance by 1, 2 or 3, groups selected from a group Q as defined above. More particularly, a substituted aryl group such as a substituted phenyl group is substituted by 1 or 2 groups selected from $C_1$-$C_6$ alkyl, halo, —$OR^8$ and —$N(R^8)_2$ wherein $R^8$ is H or $C_1$-$C_6$ alkyl, each $R^8$ being the same or different when two are present.

A $C_{3-10}$ cycloalkyl group is a saturated hydrocarbon ring having from 3 to 10 carbon atoms. A $C_{3-10}$ cycloalkyl group may be, for instance, $C_3$-$C_7$ cycloalkyl such as cyclopropyl, cyclobutyl, cyclopentyl, cyclohexyl, or cycloheptyl. Typically it is $C_3$-$C_6$ cycloalkyl, or $C_4$-$C_6$ cycloalkyl, for example cyclobutyl, cyclopentyl or cyclohexyl. In one embodiment it is cyclobutyl. A $C_{3-10}$ cycloalkyl group is unsubstituted or substituted, typically by one or more groups Q as defined above.

A 4- to 10-membered heteroaryl group or moiety is a 4- to 10-membered aromatic heterocyclic group which contains 1, 2, 3, or 4 heteroatoms selected from O, N and S. It is monocyclic or bicyclic. Typically it contains one N atom and 0, 1, 2 or 3 additional heteroatoms selected from O, S and N. It may be, for example, a monocyclic 5- to 7-membered heteroaryl group, for instance a 5- or 6-membered N-containing heteroaryl group. Examples include pyridyl, pyrazinyl, pyrimidinyl, pyridazinyl, furanyl, thienyl, pyrazolidinyl, pyrrolyl, oxadiazolyl, oxazolyl, isoxazolyl, thiazolyl, thiadiazolyl, imidazolyl and pyrazolyl groups. Furanyl, thienyl, imidazolyl, pyridyl and pyrimidyl groups are preferred. It may alternatively be a bicyclic heteroaryl group, for instance an 8- to 10-membered bicyclic heteroaryl group. Examples include quinolyl, isoquinolyl, quinazolyl, quinoxalinyl, indolyl, isoindolyl, indazolyl, imidazopyridazinyl, pyrrolopyridinyl, pyrazolopyrimidinyl and pyrrolopyrimidinyl. When substituted, a heteroaryl group (monocyclic or bicyclic) is typically substituted by one or more, e.g. 1, 2 or 3, groups selected from $C_{1-4}$ alkyl and a group Q as defined above.

A 4- to 10-membered heterocyclyl group is a monocyclic or bicyclic non-aromatic, saturated or unsaturated ring system containing 5 to 10 carbon atoms and at least one atom or group selected from N, O, S, SO, $SO_2$ and CO, more typically N or O. When the ring system is bicyclic, one ring may be saturated and one ring unsaturated. Typically, it is a $C_{4-10}$ ring system in which 1, 2 or 3 of the carbon atoms in the ring are replaced with an atom or group selected from O, S, $SO_2$, CO and NH. More typically it is a monocyclic ring, preferably a monocyclic $C_4$-$C_6$ ring. Examples include piperidyl, piperidin-2,6-dionyl, piperidin-2-onyl, piperazinyl, morpholinyl, thiomorpholinyl, S,S-dioxothiomorpholinyl, 1,3-dioxolanyl, pyrrolidinyl, imidazol-2-onyl, pyrrolidin-2-onyl, oxetanyl, tetrahydrofuranyl and tetrahydropyranyl moieties.

For the avoidance of doubt, although the above definitions of heteroaryl and heterocyclyl groups refer to an "N" atom which can be present in the ring, it will be evident to a skilled chemist that any such N atom will be protonated (or will carry a substituent as defined above) if it is attached to each of its adjacent ring atoms via a single bond. Such protonated forms are embraced within the present definitions of heteroaryl and heterocyclyl groups.

In one embodiment of formula (I) as defined above $R^2$ is a halo substituent, in particular F, at the 9-position of the benzodiazepinyl ring system. Examples of such compounds are those of the following formula (I'):

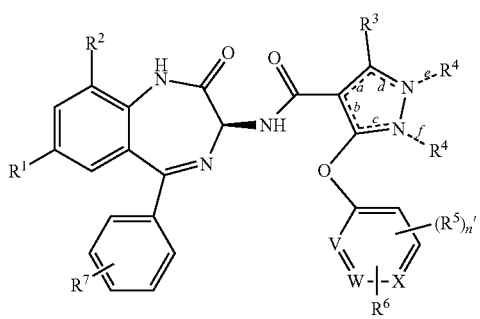

(I)

wherein $R^1$ is H or halo, $R^2$ is H or halo and the remaining groups and variables are as defined above for formula (I). Typically $R^1$ is H or F and $R^2$ is H or F. For instance, le is H or F and $R^2$ is F.

In one embodiment of formulae (I), ---a--, ---c-- and ---e-- are all bonds, with ---b--, ---d-- and ---f-- absent Such compounds have the following formula (Ia):

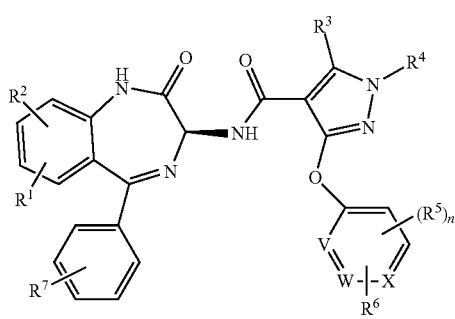

(Ia)

in which all the groups and variables are as defined above for formula (I) or (I').

In another embodiment of formula (I), ---b--, ---d-- and ---f-- are all bonds, with ---a--, ---c-- and ---e-- absent. Such compounds have the following formula (Ib):

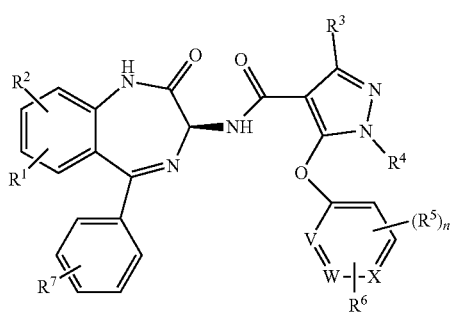

(Ib)

in which all the groups and variables are as defined above for formula (I) or (I').

In one embodiment of the above formulae (I), (I'), (Ia) and (Ib), each of V and W is CH and X is N. Examples of such structures include benzodiazepinyl pyrazoles of the following formulae (Ia') and (Ib'):

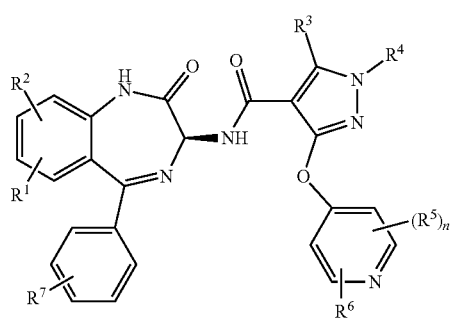

(Ia')

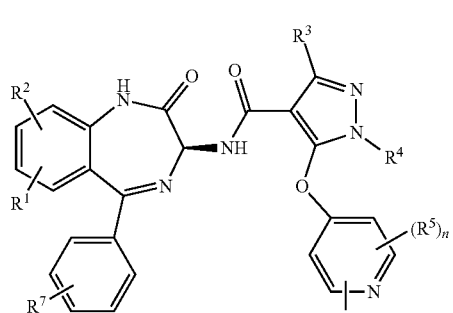

(Ib')

In the above formulae (Ia') and (Ib'), each of $R^1$ to $R^7$ and n is as defined above for formula (I) or (I').

In another embodiment of the above formulae (I), (I'), (Ia) and (Ib), V, W and X are all CH. Examples of such structures include benzodiazepinyl pyrazoles of the following formulae (Ia") and (Ib"):

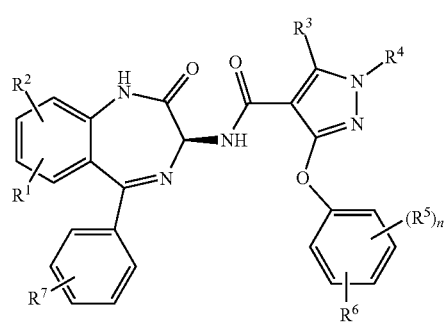

(Ia")

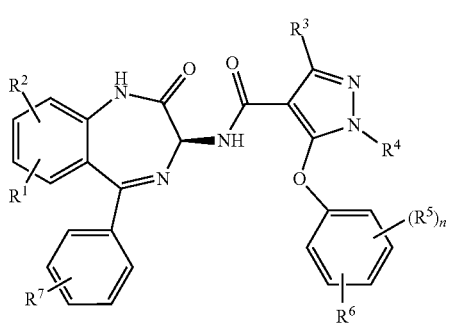

(Ib")

In formulae (Ia") and (Ib"), each of $R^1$ to $R^7$ and n is as defined above for formula (I) or (I').

In one aspect, the invention provides a compound which is a benzodiazepinyl pyrazole of the following formula (IIa):

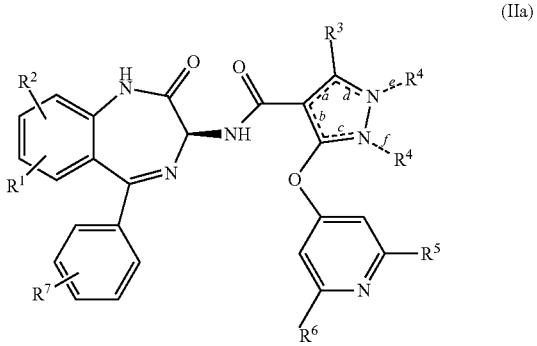

(IIa)

wherein each of the groups and variables is as defined above for formula (I) or (I'), or a pharmaceutically acceptable salt thereof.

In another aspect, the invention provides a compound which is a benzodiazepinyl pyrazole of the following formula (IIb):

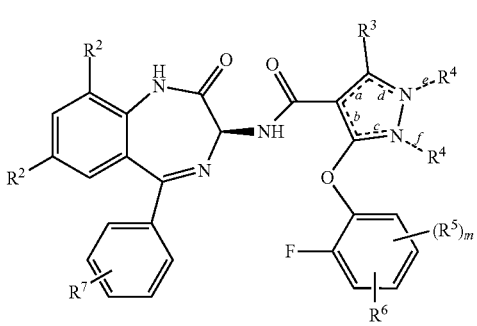

(IIb)

wherein each of the groups and variables is as defined above for formula (I) or (I') and m is 0, 1 or 2.

In one embodiment of compounds of the invention having any of the structural formulae (I), (Ia), (Ib), (Ia'), (Ib'), (Ia"), (Ib"), (IIa) or (IIb) as defined above, $R^2$ is at the 9-position of the benzodiazepinyl ring system. In this embodiment, typically $R^2$ is a halo substituent, in particular F. More typically in this embodiment, $R^1$ is H or F and $R^2$ is H or F. For instance, $R^1$ is H or F and $R^2$ is F.

When $R^1$ and $R^2$ in formula (IIa) take the same ring positions shown in formula (I') above, the resulting compound is a benzodiazepinyl pyrazole of the following formula (IIa'):

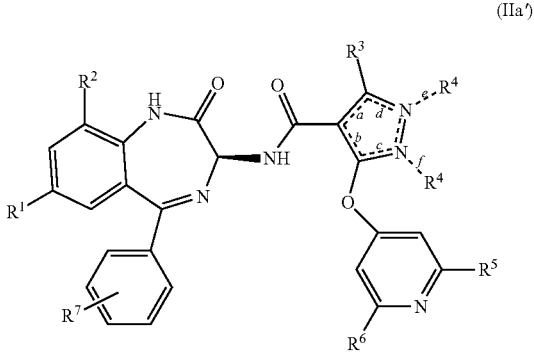

(IIa')

wherein $R^1$ is H or halo, $R^2$ is H or halo and the remaining groups and variables are as defined above for formula (IIa). Typically $R^1$ is H or F and $R^2$ is H or F. For instance, $R^1$ is H and $R^2$ is F.

Likewise, when $R^1$ and $R^2$ in formula (IIb) take the same ring positions shown in formula (I') above, the resulting compound is a benzodiazepinyl pyrazole of the following formula (IIb'):

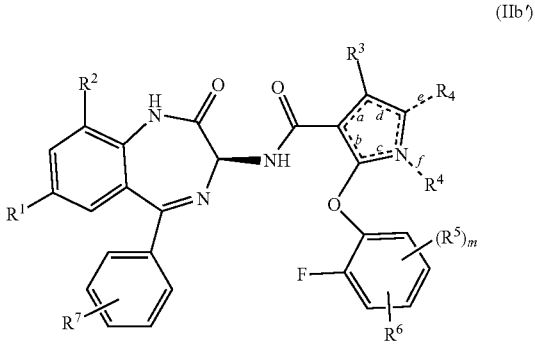

(IIb')

wherein $R^1$ is H or halo, $R^2$ is H or halo and the remaining groups and variables are as defined above for formula (IIb). Typically $R^1$ is H or F and $R^2$ is H or F. For instance, $R^1$ is H and $R^2$ is F.

In compounds of the invention having any of the structural formulae defined above, $R^3$ is a group selected from H, $C_1$-$C_6$ alkyl and —$NR^8R^9$, wherein each of $R^8$ and $R^9$ is independently H or a group selected from $C_1$-$C_6$ alkyl, $C_3$-$C_6$ cycloalkyl and 4- to 10-membered heterocyclyl, the group being unsubstituted or substituted. Typically $R^8$ is H and $R^9$ is H or a group selected from $C_1$-$C_6$ alkyl, $C_3$-$C_6$ cycloalkyl and 4- to 10-membered heterocyclyl, the group being unsubstituted or substituted. In one embodiment $R^8$ is H and $R^9$ is H or $C_1$-$C_6$ alkyl.

In compounds of the invention having any of the structural formulae defined above, $R^4$ is H or a group selected from $C_1$-$C_6$ alkyl, $C_3$-$C_6$ cycloalkyl and 4- to 10-membered heterocyclyl, the group being unsubstituted or substituted. In one embodiment $R^4$ is a group selected from $C_1$-$C_6$ alkyl, $C_3$-$C_6$ cycloalkyl and 4- to 10-membered heterocyclyl, the group being unsubstituted or substituted. Typically $R^4$ is a group selected from $C_1$-$C_6$ alkyl (such as $C_1$-$C_3$ alkyl), $C_3$-$C_6$ cycloalkyl (such as cyclopropyl) and 4- to 10-membered heterocyclyl (for instance, an O-containing heterocyclyl group such as oxetanyl, tetrahydrofuranyl or tetrahydropyranyl).

In compounds of the invention having any of the structural formulae defined above, $R^5$ is H or halo, in particular F.

In compounds of the invention having any of the structural formulae (I), (I'), (Ia), (Ib), (Ia'), (Ib'), (Ia") or (Ib") defined above there may be one, two or three groups $R^5$, which are the same or different when more than one is present. At least one group $R^5$ is typically F. The or each $R^5$ is bonded to any available ring carbon atom of the six-membered ring to which it is attached.

In one embodiment $R^6$ is H, n is 2, one $R^5$ is F and the other $R^5$ is F or Cl. In another embodiment $R^6$ is H, n is 3, two groups $R^5$ are each F and the other $R^5$ is Cl.

In one embodiment at least one $R^5$ is bonded ortho to the ring carbon bearing the bond that links the six-membered ring to the adjacent O atom, i.e. one $R^5$ is bonded at ring position 2 or 6. For instance, n is 1 and $R^5$ is bonded at ring position 2 or 6; or n is 2 and the two groups $R^5$ are bonded at ring positions 2 and 4, or 2 and 6, or 4 and 6. In such embodiments the or each ortho-bonded group $R^5$ is typically F.

In compounds of the invention having any of the structural formulae (I), (I'), (Ia), (Ib), (Ia'), (Ib'), (Ia"), (Ib"), (IIb) or (IIb') defined above, $R^6$ is bonded at any available ring carbon atom not occupied by $R^5$. For instance, it is bonded at ring position 4 (i.e. para to the ring carbon bearing the bond that links the six-membered ring to the adjacent O atom; or it is bonded at ring position 3 or 5, i.e. meta to the ring carbon bearing the bond that links the six-membered ring to the adjacent O atom.

Examples of the six-membered ring bound by groups $R^5$ and $R^6$ in compounds of the above structural formulae (I), (I'), (Ia), (Ib), (Ia'), (Ib'), (Ia") and (Ib") include the following structures (i) to (v):

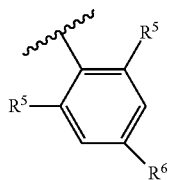

(i)

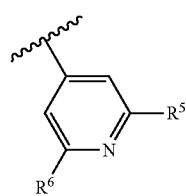

(ii)

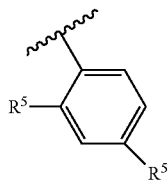

(iii)

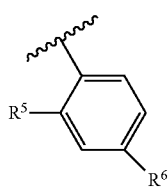

(iv)

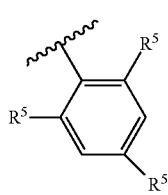

(v)

In compounds of the invention having any of the structural formulae defined above, $R^6$ is —$OR^8$, —$NR^8R^9$ or —$R^8$ wherein each of $R^8$ and $R^9$ is H or a group selected from $C_1$-$C_6$ alkyl, $C_3$-$C_6$ cycloalkyl and 4- to 10-membered heterocyclyl, the group being unsubstituted or substituted. Typically $R^6$ is H, $C_1$-$C_6$ alkyl, —$OR^8$ or —$NR^8R^9$ wherein $R^8$ is $C_1$-$C_6$ alkyl (such as $C_1$-$C_3$ alkyl), $C_3$-$C_6$ cycloalkyl (such as cyclopropyl or cyclobutyl) and $R^9$ is H or $C_1$-$C_6$ alkyl, the alkyl and cycloalkyl groups being unsubstituted or substituted. More typically $R^6$ is $C_1$-$C_6$ alkyl, —$OR^8$ or —$NR^8R^9$ wherein $R^8$ is unsubstituted $C_1$-$C_6$ alkyl (such as methyl, ethyl or i-propyl) or $C_3$-$C_6$ cycloalkyl (such as cyclopropyl or cyclobutyl), the cycloalkyl group being unsubstituted or substituted by unsubstituted $C_1$-$C_3$ alkyl (such as methyl), and $R^9$ is $C_1$-$C_6$ alkyl or H.

In one embodiment $R^6$ is $C_1$-$C_6$ alkyl or a group —$NR^8R^9$ in which $R^8$ and $R^9$ are the same or different and are each H or $C_1$-$C_6$ alkyl, n is 1 or 2 and each $R^5$ is F. $C_1$-$C_6$ in these embodiments is typically methyl or ethyl.

Specific compounds of the invention include the following:

5-(2,6-Difluoro-4-methylphenoxy)-1-ethyl-N-[(3S)-2-oxo-5-phenyl-1,3-dihydro-1,4-benzodiazepin-3-yl]pyrazole-4-carboxamide;

5-(2-Fluoro-4-methylphenoxy)-1-(oxan-4-yl)-N-[(3S)-2-oxo-5-phenyl-1,3-dihydro-1,4-benzodiazepin-3-yl]pyrazole-4-carboxamide;

5-(4-Chloro-2-fluorophenoxy)-N-[(3S)-9-fluoro-2-oxo-5-phenyl-1,3-dihydro-1,4-benzodiazepin-3-yl]-1-(oxetan-3-yl)pyrazole-4-carboxamide;

5-(4-Chloro-2-fluorophenoxy)-N-[(3S)-9-fluoro-2-oxo-5-phenyl-1,3-dihydro-1,4-benzodiazepin-3-yl]-1-(oxan-4-yl)pyrazole-4-carboxamide;

5-(4-Chloro-2,6-difluorophenoxy)-N-[(3S)-9-fluoro-2-oxo-5-phenyl-1,3-dihydro-1,4-benzodiazepin-3-yl]-1-(oxetan-3-yl)pyrazole-4-carboxamide;

5-(4-Chloro-2,6-difluorophenoxy)-N-[(3S)-9-fluoro-2-oxo-5-phenyl-1,3-dihydro-1,4-benzodiazepin-3-yl]-1-(oxan-4-yl)pyrazole-4-carboxamide;

and the pharmaceutically acceptable salts thereof.

The compounds of the invention may contain asymmetric or chiral centres, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Compounds of Formula (I) containing one or more chiral centre may be used in enantiomerically or diastereoisomerically pure form, or in the form of a mixture of isomers.

The present invention embraces all geometric and positional isomers of compounds of the invention as defined above. For example, if a compound of the invention incorporates a double bond or a fused ring, the cis- and transforms, as well as mixtures thereof, are embraced within the scope of the invention. Both the single positional isomers and mixture of positional isomers are also within the scope of the present invention.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol tautomerizations. Valence tautomers include interconversions by reorganization of some of the bonding electrons.

Compounds of the invention can be prepared by the synthetic methods described in the Examples that follow, or by analogy with such methods using appropriate starting materials and methodologies familiar to the skilled chemist.

A benzodiazepine derivative of formula (I) can be converted into a pharmaceutically acceptable salt thereof, and a salt can be converted into the free compound, by conventional methods. For instance, a benzodiazepine derivative of formula (I) can be contacted with a pharmaceutically acceptable acid to form a pharmaceutically acceptable salt. A pharmaceutically acceptable salt is a salt with a pharmaceutically acceptable acid or base.

Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

Compounds of the present invention have been found in biological tests to be inhibitors of respiratory syncytial virus (RSV). They possess a combination of potent anti-RSV activity with good bioavailability and good physicochemical properties. This combination of properties makes the compounds therapeutically useful and superior as drug candidates to many compounds disclosed in the prior art references discussed earlier.

Accordingly, the present invention further provides a compound which is a benzodiazepine derivative of formula (I), as defined above, or a pharmaceutically acceptable salt thereof, for use in a method of treating the human or animal body by therapy.

The invention also provides a compound of the invention as defined above for use in a method treating or preventing an RSV infection. Still further, the present invention provides the use of a compound of the invention as defined above in the manufacture of a medicament for use in treating or preventing an RSV infection. A subject suffering from or susceptible to an RSV infection may thus be treated by a method comprising the administration thereto of a compound of the invention as defined above. The condition of the subject may thereby be improved or ameliorated.

The RSV infection is typically a respiratory tract infection. The RSV infection may be an infection in a child, for instance a child under ten years of age or an infant under two years of age. In one embodiment the invention provides a compound as defined above for use in treating or preventing an RSV infection in paediatric patients. Alternatively the infection may be an infection in a mature or elderly adult, for instance an adult over 60 years of age, an adult over 70 years of age, or an adult over 80 years of age. The invention further provides a compound for use in treating or preventing an RSV infection in geriatric patients.

The RSV infection may be an infection in an immunocompromised individual or an individual suffering from COPD or CHF. In another embodiment, the RSV infection is an infection in a non-compromised individual, for instance an individual who is otherwise healthy.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection, infusion, or by inhalation or nebulaisation. The compound is preferably given by oral administration.

The dosage depends on a variety of factors including the age, weight and condition of the patient and the route of administration. Daily dosages can vary within wide limits and will be adjusted to the individual requirements in each particular. Typically, however, the dosage adopted for each route of administration when a compound is administered alone to adult humans is 0.0001 to 650 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A unit dose form such as a tablet or a capsule will usually contain 1-250 mg of active ingredient. For example, a compound of formula (I) could be administered to a human patient at a dose of between 100-250 mg either once a day, twice or three times a day. For example, a compound of formula (I) could be administered to a human patient at a dose of between 100-250 mg either once a day, twice or three times a day.

The compounds of formula (I) and pharmaceutically acceptable salts thereof may be used on their own. Alternatively, they may be administered in the form of a pharmaceutical composition. The present invention therefore also provides a pharmaceutical composition comprising a compound of formula (I) or a pharmaceutically acceptable salt thereof as hereinbefore defined, in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The compounds of the invention may be administered in a variety of dosage forms. Thus, they can be administered orally, for example as tablets, troches, lozenges, aqueous or oily suspensions, solutions, dispersible powders or granules. The compounds of the invention may also be administered parenterally, whether subcutaneously, intravenously, intramuscularly, intrasternally, transdermally, by infusion techniques or by inhalation or nebulaisation. The compounds may also be administered as suppositories.

Solid oral forms of the pharmaceutical composition of the invention may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures;

dyestuffs; sweeteners; wetting agents, such as lecithin, polysorbates, laurylsulfates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride. Further suitable carriers for suspensions include sterile water, hydroxypropylmethyl cellulose (HPMC), polysorbate 80, polyvinylpyrrolidone (PVP), aerosol AOT (i.e. sodium 1,2-bis(2-ethylhexoxycarbonyl)ethanesulphonate), pluronic F127 and/or captisol (i.e. sulfobutylether-beta-cyclodextrin).

The compounds of the invention may, for example, be formulated as aqueous suspensions in a carrier selected from:
(i) 0.5% w/v hydroxypropylmethyl cellulose (HPMC)/ 0.1% w/v polysorbate 80;
(ii) 0.67% w/v polyvinylpyrrolidone (PVP)/0.33% w/v aerosol AOT (sodium 1,2-bis(2-ethylhexoxycarbonyl) ethanesulphonate);
(iii) 1% w/v pluronic F 127; and
(iv) 0.5% w/v polysorbate 80.

The carriers may be prepared by standard procedures known to those of skill in the art. For example, each of the carriers (i) to (iv) may be prepared by weighing the required amount of excipient into a suitable vessel, adding approximately 80% of the final volume of water and magnetically stirring until a solution is formed. The carrier is then made up to volume with water. The aqueous suspensions of compounds of formula I may be prepared by weighing the required amount of a compound of formula I into a suitable vessel, adding 100% of the required volume of carrier and magnetically stirring.

Solutions for injection or infusion may contain as carrier, for example, sterile water or preferably they may be in the form of sterile, aqueous, isotonic saline solutions.

The compounds of the invention may also be administered in conjunction with other compounds used for the treatment of viral infections. Thus, the invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment or prevention of a viral infection, particularly infection by RSV.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

Suitable therapeutic agents for use in the combination therapies include (i) RSV fusion inhibitors
(ii) other RSV nucleocapsid (N)-protein inhibitors;
(iii) other RSV protein inhibitors, such as those that inhibit the phosphoprotein (P) protein and large (L) protein;
(iv) nucleoside or polymerase inhibitors that inhibit the L protein;
(v) anti-RSV monoclonal antibodies, such as the F-protein antibodies;
(vi) immunomodulating toll-like receptor compounds;
(vii) other respiratory virus anti-virals, such as anti-influenza and anti-rhinovirus compounds; and/or
(viii) anti-inflammatory compounds.

The RSV nucleocapsid (N)-protein plays a pivotal role in viral transcription and replication, mediating the interaction between the genomic RNA and the virally encoded RNA-dependent RNA polymerase. The RSV P- and L-proteins are components of RSV's virally encoded RNA-dependent RNA polymerase.

According to a further aspect of the invention, there is provided a compound of the formula (I) or a pharmaceutically acceptable salt thereof as hereinbefore defined in combination with one or more of the therapeutic agents listed as (i) to (vi) above for use in the treatment of RSV.

The Examples that follow serve to illustrate the invention further. The Preparatory Examples relate to the preparation of starting materials and intermediates used to prepare the compounds of the Examples. Neither the Examples nor the Preparatory Examples limit the invention in any way.

EXAMPLES

Reagents were obtained from commercial sources and were used without further purification. All temperatures are in ° C. TLC was performed on aluminium backed silica gel plates with fluorescence indicator at 254 nM (median pore size 60 Å). Flash column chromatography was performed using a Biotage Isolera One system using KP-Sil or Ultra silica gel columns unless otherwise noted. NMR spectra were recorded on a 400 MHz spectrometer at ambient probe temperature (nominal 295 K). Chemical shifts (δ) are given in ppm and calibrated by using the residual peak of the solvent as the internal standard (CDCl$_3$, δ$_H$=7.26 ppm, δ$_C$=77.16 ppm; DMSO-d$_6$, δ$_H$=2.50 ppm, δ$_C$=39.52 ppm). Coupling constants are given in Hertz (Hz). LRMS were recorded using an Advion Plate Express expression$^L$ compact mass spectrometer equipped with an APCI ion source.

Preparatory examples (3S)-3-amino-5-phenyl-1,3-dihydro-1,4-benzodiazepin-2-one and (3S)-3-amino-9-fluoro-5-phenyl-1,3-dihydro-1,4-benzodiazepin-2-one were prepared using methods described in WO/2004/026843, WO/2005/090319, and WO/2017/015449.

Abbreviations

| | |
|---|---|
| APCI | Atmospheric pressure chemical ionization |
| DMF | N,N-Dimethylformamide |
| DMSO | Dimethyl sulfoxide |
| h | Hour(s) |
| HATU | 1-[Bis(dimethylamino)methylene]-1H-1,2,3-triazolo[4,5-b]pyridinium 3-oxid hexafluorophosphate, N-[(dimethylamino)-1H-1,2,3-triazolo-[4,5-b]pyridin-1-ylmethylene]-N-methylmethanaminium hexafluorophosphate N-oxide |
| LRMS | Low resolution mass spectrometry |
| rt | room temperature |
| THF | Tetrahydrofuran |

Preparatory Examples

1A Ethyl 5-amino-1-ethylpyrazole-4-carboxylate

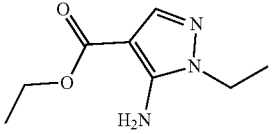

A suspension of ethyl (ethoxymethylene)cyanoacetate (10.50 g, 62.06 mmol) in anhydrous EtOH (120 mL) was prepared, and ethylhydrazine oxalate (9.32 g, 62.06 mmol) added, followed by addition of NEt$_3$ (17.3 mL, 124.1 mmol) by syringe over 15 minutes. The reaction was heated at 50° C. for 5 h, then stirred at rt for 16 h. The volatiles were removed under reduced pressure, and the residue dissolved in EtOAc (100 mL). The crude was washed with water (2×60 mL) and brine (60 mL), dried (MgSO$_4$) and the solvent was removed under reduced pressure. The residue was purified by flash chromatography (30% EtOAc:heptane) to afford a yellow solid (5.16 g, 45%). LRMS: 184.0 [M+H]$^+$; TLC (EtOAc) R$_f$=0.63.

2A Ethyl 5-chloro-1-ethylpyrazole-4-carboxylate

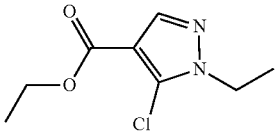

t-Butyl nitrite (5.19 mL, 43.7 mmol) was added to a cooled (0° C.) solution of copper (I) chloride (3.24 g, 32.7 mmol) in MeCN (90 mL) under nitrogen. Intermediate 1A (5.00 g, 27.3 mmol) was added portionwise over 30 minutes, the reaction stirred at 0° C. for 1 h, then heated at 65° C. for 40 minutes. The reaction was cooled to rt and was poured into 6 M aq HCl (100 mL), and extracted with CH$_2$Cl$_2$ (100 mL, then 3×50 mL). The combined organics were dried (MgSO$_4$), the solvent removed under reduced pressure and the residue purified by flash chromatography (0-10% EtOAc:heptane) to afford a colourless oil (2.87 g, 52%). $^1$H NMR (400 MHz, DMSO-d$_6$) δ 7.98 (s, 1H), 4.23 (q, J=7.1 Hz, 2H), 4.19 (q, J=7.3 Hz, 2H) 1.33 (t, J=7.2 Hz, 3H), 1.27 (t, J=7.1 Hz, 3H). LRMS: 202.9 [M+H]$^+$.

3A Ethyl 5-bromo-1-(oxan-4-yl)pyrazole-4-carboxylate

4A Ethyl 3-bromo-1-(oxan-4-yl)pyrazole-4-carboxylate

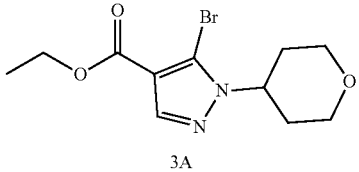

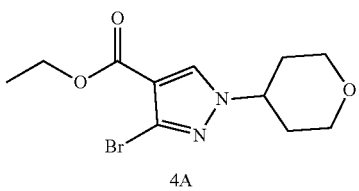

Oxan-4-yl 4-methylbenzenesulfonate (1.67 g, 6.53 mmol) was added to a solution of ethyl 3-bromo-1H-pyrazole-4-carboxylate (1.30 g, 5.93 mmol) and Cs$_2$CO$_3$ (2.63 g, 8.01 mmol) in DMF (10 mL) and heated at 80° C. for 16 h. Upon cooling to rt, water (40 mL) was added and the mixture extracted with EtOAc (3×20 mL). The organics were washed with water and brine (20 mL each), dried (Na$_2$SO$_4$) and the solvent removed under reduced pressure. Purification by flash chromatography (10-80% EtOAc:heptane) afforded intermediate 3A as a white solid (445 mg, 25%). $^1$H NMR (400 MHz, DMSO-d$_6$) δ 8.05 (s, 1H), 4.66 (tt, J=11.3, 4.3 Hz, 1H), 4.24 (q, J=7.1 Hz, 2H), 4.01-3.91 (m, 2H), 3.50 (td, J=12.0, 2.1 Hz, 2H), 2.08-1.94 (m, 2H) 1.83 (ddd, J=12.6, 4.4, 2.0 Hz, 2H), 1.27 (t, J=7.1 Hz, 3H). LRMS: 303.0/305.0 [M+H]$^+$. Intermediate 4A (second eluting regioisomer) was obtained as a white solid (1.02 g, 57%). $^1$H NMR (400 MHz, DMSO-d$_6$) δ 8.43 (s, 1H), 4.45 (dd, J=10.5, 5.0 Hz, 1H), 4.22 (q, J=7.1 Hz, 2H), 4.00-3.88 (m, 2H), 3.48-3.36 (m, 2H), 2.04-1.83 (m, 4H), 1.27 (t, J=7.1 Hz, 3H). LRMS: 303.4/305.4 [M+H]$^+$.

5A Ethyl 5-bromo-1-(oxetan-3-yl)pyrazole-4-carboxylate

6A Ethyl 3-bromo-1-(oxetan-3-yl)pyrazole-4-carboxylate

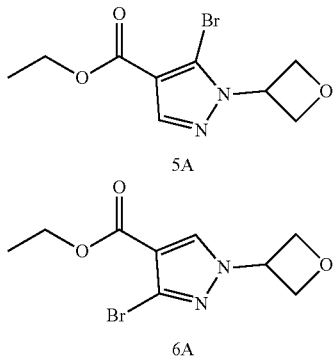

Prepared by an analogous procedure to that described for intermediate 3A with ethyl 3-bromo-1H-pyrazole-4-carboxylate (1.70 g, 7.76 mmol), oxetan-3-yl 4-methylbenzene sulfonate (1.95 g, 8.50 mmol) and $Cs_2CO_3$ (3.43 g, 10.48 mmol) and heating at 90° C. for 22 h. Purification by flash chromatography (10-100% EtOAc:heptane) afforded intermediate 5A (first eluting regioisomer) as a white solid (640 mg, 30%). $^1$H NMR (400 MHz, DMSO-$d_6$) δ 8.15 (s, 1H), 5.75 (tt, J=7.4, 6.2 Hz, 1H), 4.98-4.85 (m, 4H), 4.24 (q, J=7.1 Hz, 2H), 1.28 (t, J=7.1 Hz, 3H). LRMS: 275.5/277.5 [M+H]$^+$. Intermediate 6A: second eluting regioisomer, white solid (1.06 g, 50%). $^1$H NMR (400 MHz, DMSO-$d_6$) δ 8.50 (s, 1H), 5.60 (tt, J=7.5, 6.1 Hz, 1H), 4.94-4.77 (m, 4H), 4.23 (q, J=7.1 Hz, 2H), 1.27 (t, J=7.1 Hz, 3H). LRMS: 275.5/277.5 [M+H]$^+$.

7A Ethyl 5-(2-fluoro-4-methylphenoxy)-1-(oxan-4-yl)pyrazole-4-carboxylate

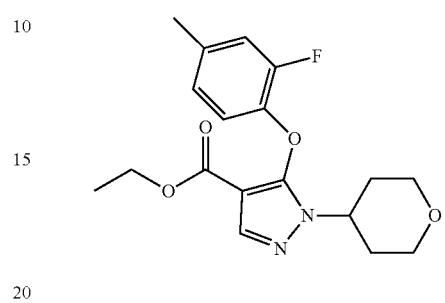

A solution of intermediate 3A (150 mg, 0.49 mmol), 2-fluoro-4-methylphenol (68.7 mg, 0.54 mmol) and $Cs_2CO_3$ (324 mg, 0.99 mmol) in 1-methyl-2-pyrrolidinone (2 mL) was heated in a sealed vial at 135° C. for 21 h. The reaction was cooled to rt, diluted with water (10 mL) and extracted with EtOAc (3×15 mL). The combined organics were washed with water (2×15 mL) and brine (15 mL), dried ($Na_2SO_4$), and the solvent removed under reduced pressure. The residue was purified by flash chromatography (0-30% EtOAc:heptane) to afford a white solid (100 mg, 58%). $^1$H NMR (400 MHz, DMSO-$d_6$) δ 7.94 (s, 1H), 7.28-7.15 (m, 1H), 6.98-6.86 (m, 1H), 6.74 (t, J=8.6 Hz, 1H), 4.54-4.40 (m, 1H), 4.04-3.86 (m, 4H), 3.51-3.39 (m, 2H), 2.27 (s, 3H), 2.10-1.95 (m, 2H), 1.84-1.72 (m, 2H), 0.96 (t, J=7.1 Hz, 3H). LRMS: 349.1 [M+H]$^+$.

The following intermediate compounds were prepared by the same general procedure described for intermediate 7A.

| Preparatory example | Structure | Name | $^1$H NMR δ (400 MHz, DMSO-$d_6$) | LRMS [M + H]$^+$/ TLC |
|---|---|---|---|---|
| 8A | (structure) | Ethyl 5-(2,6-difluoro-4-methylphenoxy)-1-ethylpyrazole-4-carboxylate | — | 311.1; $R_f$ = 0.58 (1:2 EtOAc:heptane) |
| 9A | (structure) | 5-(4-Chloro-2-fluorophenoxy)-1-(oxetan-3-yl)pyrazole-4-carboxylic acid | 8.08 (d, J = 0.5 Hz, 1H), 7.66 (dd, J = 10.9, 2.5 Hz, 1H), 7.25-7.15 (m, 1H), 6.98 (t, J = 9.0 Hz, 1H), 5.68-5.55 (m, 1H), 4.97-4.77 (m, 4H), 3.99 (q, J = 7.1 Hz, 2H), 0.98 (t, J = 7.1 Hz, 3H). | 341.3. |

| Preparatory example | Structure | Name | $^1$H NMR δ (400 MHz, DMSO-$d_6$) | LRMS [M + H]$^+$/ TLC |
| --- | --- | --- | --- | --- |
| 10A | 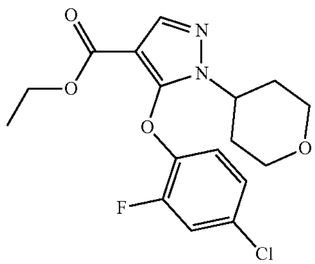 [SMILES: CCOC(=O)c1cnn(C2CCOCC2)c1Oc1ccc(Cl)cc1F] | Ethyl 5-(4-chloro-2-fluorophenoxy)-1-(oxan-4-yl)pyrazole-4-carboxylate | 7.97 (s, 1H), 7.67 (dd, J = 10.9, 2.5 Hz, 7.24-7.16 (m, 1H), 6.94 (t, J = 8.9 Hz, 1H), 4.57-4.45 (m, 1H), 4.03-3.86 (m, 5H), 3.44 (td, J = 12.0, 2.0 Hz, 2H), 2.10-1.95 (m, 2H), 1.85-1.75 (m, 2H), 0.97 (t, J = 7.1 Hz, 3H). | 369.1. |
| 11A | 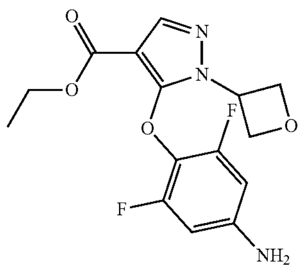 [SMILES: CCOC(=O)c1cnn(C2COC2)c1Oc1c(F)cc(N)cc1F] | Ethyl 5-(4-amino-2,6-difluorophenoxy)-1-(oxetan-3-yl)pyrazole-4-carboxylate | 7.93 (d, J = 0.4 Hz, 1H), 6.23 (d, J = 11.3 Hz, 2H), 5.82-5.68 (m, 1H), 5.60 (s, 2H), 4.90 (d, J = 7.0 Hz, 4H), 4.01 (q, J = 7.1 Hz, 2H), 1.08 (t, J = 7.1 Hz, 3H). | 340.3. |
| 12A | 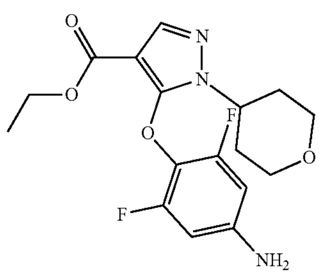 [SMILES: CCOC(=O)c1cnn(C2CCOCC2)c1Oc1c(F)cc(N)cc1F] | Ethyl 5-(4-amino-2,6-difluorophenoxy)-1-(oxan-4-yl)pyrazole-4-carboxylate | 7.80 (s, 1H). 6.25 (d, J = 11.2 Hz, 2H), 5.59 (s, 2H), 4.67-4.57 (m, 1H), 4.05-3.89 (m, 3H), 3.55-3.40 (m, 2H), 2.08-1.90 (m, 3H), 1.84-1.77 (m, 2H), 1.07 (t, J = 7.1 Hz, 3H). | 368.3. |

13A Ethyl 5-(4-chloro-2,6-difluorophenoxy)-1-(oxetan-3-yl)pyrazole-4-carboxylate

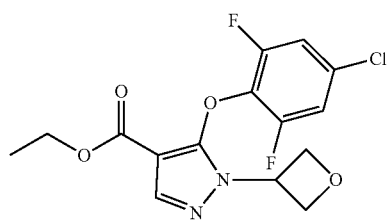 [SMILES: CCOC(=O)c1cnn(C2COC2)c1Oc1c(F)cc(Cl)cc1F]

Prepared by an analogous procedure to intermediate 2A using copper (II) chloride (25.0 mg, 0.19 mmol), t-butyl nitrite (0.03 mL, 0.22 mmol), intermediate 11A (63 mg, 0.15 mmol) in MeCN (8 mL) with stirring at 0° C. for 20 minutes then rt for 4 hours. Yellow oil (20 mg, 38%). LRMS: 359.1 [M+H]$^+$; TLC (1:1 EtOAc:heptane) $R_f$=0.65.

14A Ethyl 5-(4-chloro-2,6-difluorophenoxy)-1-(oxan-4-yl)pyrazole-4-carboxylate

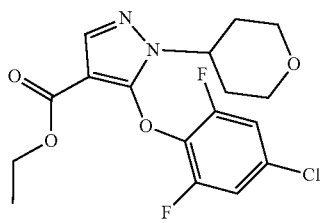 [SMILES: CCOC(=O)c1cnn(C2CCOCC2)c1Oc1c(F)cc(Cl)cc1F]

Prepared by an analogous procedure to intermediate 2A using copper (II) chloride (76.4 mg, 0.57 mmol), t-butyl nitrite (0.08 mL, 0.68 mmol) and intermediate 12A (167 mg, 0.45 mmol) in MeCN (16 mL) with stirring at 0° C. for 30 minutes and rt for 3 hours. White solid (27 mg, 15%). LRMS: 387.3 [M+H]$^+$; TLC (1:1 EtOAc:heptane) $R_f$=0.83.

15A 5-(2,6-Difluoro-4-methylphenoxy)-1-ethylpyrazole-4-carboxylic Acid

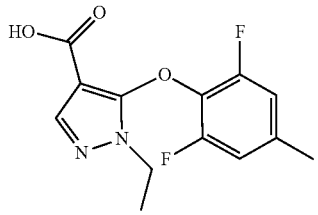 [SMILES: CCn1ncc(C(=O)O)c1Oc1c(F)cc(C)cc1F]

A solution of intermediate 8A (70 mg, 0.230 mmol) and LiOH (1 M aq; 1.8 mL, 1.8 mmol) in THF:MeOH (1:1; 6 mL) was heated at 55° C. for 3 h. The volatiles were removed under reduced pressure, the residue acidified to pH 2 with HCl (1 M aq.) then extracted with EtOAc (3×10 mL). The combined organic extracts were washed with water and brine (10 mL each), dried (MgSO$_4$), and the solvent was removed under reduced pressure to afford a white solid (58 mg, 91%). $^1$H NMR (400 MHz, DMSO-d$_6$) δ 7.73 (s, 1H), 7.02 (d, J=9.8 Hz, 2H), 4.12 (q, J=7.3 Hz, 2H), 2.27 (s, 3H), 1.34 (t, J=7.2 Hz, 3H). LRMS: 283.0 [M+H]$^+$.

The following intermediate compounds were prepared in an analogous manner to intermediate 15A.

| Preparatory example | Structure | Name | $^1$H NMR δ (400 MHz, DMSO-d$_6$) | LRMS [M + H]$^+$/ TLC |
|---|---|---|---|---|
| 16A | 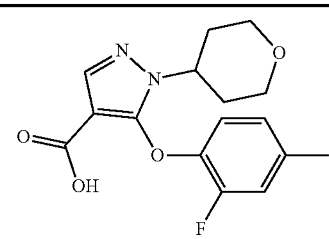 | 5-(2-Fluoro-4-methylphenoxy)-1-(oxan-4-yl)pyrazole-4-carboxylic acid | 12.25 (s, 1H), 7.88 (s, 1H), 7.19 (dd, J = 12.5, 2.0 Hz, 1H), 6.96-6.82 (m, 1H), 6.71 (t, J = 8.6 Hz, 1H), 4.51-4.33 (m, 1H), 3.98-3.83 (m, 2H), 3.51-3.35 (m, 2H), 2.26 (s, 3H), 2.08-1.93 (m, 2H), 1.87-1.66 (m, 2H). | 321.1 |
| 17A | 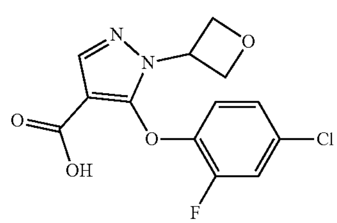 [SMILES: O=C(O)c1cnn(C2COC2)c1Oc1ccc(Cl)cc1F] | 5-(4-Chloro-2-fluorophenoxy)-1-(oxetan-3-yl)pyrazole-4-carboxylic acid | 12.45 (s, 1H), 8.02 (s, 1H), 7.64 (dd, J = 10.9, 2.5 Hz, 1H), 7.28-7.14 (m, 1H), 6.93 (t, J = 8.9 Hz, 1H), 5.65-5.50 (m, 1H), 4.96-4.80 (m, 4H). | 313.3. |
| 18A | 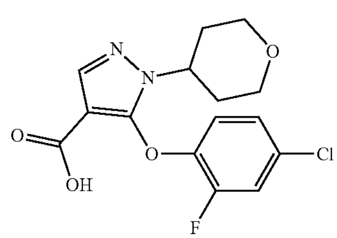 [SMILES: O=C(O)c1cnn(C2CCOCC2)c1Oc1ccc(Cl)cc1F] | 5-(4-Chloro-2-fluorophenoxy)-1-(oxan-4-yl)pyrazole-4-carboxylic acid | 12.36 (s, 1H), 7.90 (s, 1H), 7.65 (dd, J = 10.9, 2.5 Hz, 1H), 7.23-7.15 (m, 1H), 6.91 (t, J = 8.9 Hz, 1H), 4.54-4.44 (m, 1H), 3.96-3.88 (m, 2H), 3.43 (s, 2H), 2.09-1.96 (m, 2H), 1.83-1.73 (m, 2H). | 321.1. |
| 19A | 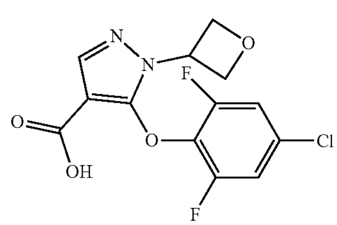 [SMILES: O=C(O)c1cnn(C2COC2)c1Oc1c(F)cc(Cl)cc1F] | 5-(4-Chloro-2,6-difluorophenoxy)-1-(oxetan-3-yl)pyrazole-4-carboxylic acid | 12.47 (s, 1H), 7.93 (s, 1H), 7.52 (d, J = 8.3 Hz, 2H), 5.91-5.72 (m, 1H), 5.03-4.79 (m, 4H). | 331.1 |

| Preparatory example | Structure | Name | $^1$H NMR δ (400 MHz, DMSO-$d_6$) | LRMS [M + H]$^+$/ TLC |
|---|---|---|---|---|
| 20A | 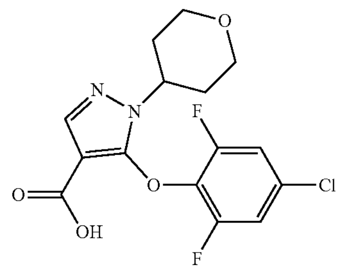 [SMILES: O=C(O)c1cnn(C2CCOCC2)c1Oc1c(F)cc(Cl)cc1F] | 5-(4-Chloro-2,6-difluorophenoxy)-1-(oxan-4-yl)pyrazole-4-carboxylic acid | | 369.1; $R_f$ = 0.78 (1:1 EtOAc: heptane) |

Examples

1. 5-(2,6-Difluoro-4-methylphenoxy)-1-ethyl-N-[(3S)-2-oxo-5-phenyl-1,3-dihydro-1,4-benzodiazepin-3-yl]pyrazole-4-carboxamide

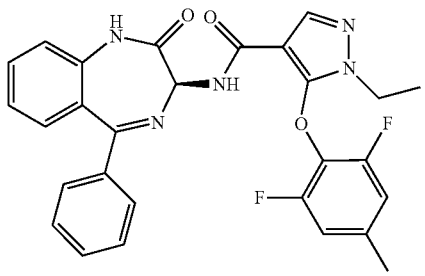 [SMILES: CCn1ncc(C(=O)N[C@H]2N=C(c3ccccc3)c3ccccc3NC2=O)c1Oc1c(F)cc(C)cc1F]

NEt$_3$ (0.04 mL, 0.32 mmol) and HATU (66.6 mg, 0.18 mmol) were added to a solution of intermediate 15A (49.4 mg, 0.18 mmol) and (3S)-3-amino-5-phenyl-1,3-dihydro-1,4-benzodiazepin-2-one (40.0 mg, 0.16 mmol) in DMF (1 mL) and the reaction was stirred at rt for 2 h 45 minutes. Water (20 mL) was added, resulting in the formation of a precipitate, which was collected by filtration, washing with water (5 mL). The precipitate was dissolved in EtOAc (20 mL), dried (MgSO$_4$), concentrated under reduced pressure and purified by flash chromatography (50-100% EtOAc: heptane) to afford a white solid (66 mg, 80%). $^1$H NMR (400 MHz, DMSO-$d_6$) δ 10.85 (s, 1H), 9.02 (d, J=8.2 Hz, 1H), 8.34 (s, 1H), 7.65-7.59 (m, 1H), 7.55-7.37 (m, 5H), 7.31-7.16 (m, 3H), 6.93 (d, J=9.8 Hz, 2H), 5.23 (d, J=8.2 Hz, 1H), 4.12 (q, J=7.2 Hz, 2H), 2.21 (s, 3H), 1.35 (t, J=7.2 Hz, 3H). LRMS: 516.5 [M+H]$^+$.

The following compounds of the invention were prepared with (3S)-3-amino-5-phenyl-1,3-dihydro-1,4-benzodiazepin-2-one or (3S)-3-amino-9-fluoro-5-phenyl-1,3-dihydro-1,4-benzodiazepin-2-one by the procedure described for the compound of Example 1.

| Example | Structure | Name | $^1$H NMR δ (400 MHz, DMSO-$d_6$) | LRMS [M + H]$^+$ |
|---|---|---|---|---|
| 2 | 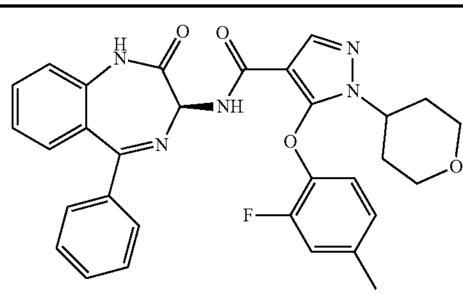 | 5-(2-Fluoro-4-methylphenoxy)-1-(oxan-4-yl)-N-[(3S)-2-oxo-5-phenyl-1,3-dihydro-1,4-benzodiazepin-3-yl]pyrazole-4-carboxamide | 10.85 (s, 1H), 8.98 (d, J = 8.1 Hz, 1H), 8.42 (s, 1H), 7.64-7.58 (m, 1H), 7.55-7.38 (m, 5H), 7.35-7.08 (m, 4H), 6.91-6.78 (m, 1H), 6.64 (t, J = 8.6 Hz, 1H), 5.27 (d, J = 8.0 Hz, 1H), 4.45-4.28 (m, 1H), 3.92 (dd, J = 11.4, 4.4 Hz, 2H), 3.46-3.36 (m, 2H), 2.22 (s, 3H), 2.13-2.00 (m, 2H), 1.82-1.63 (m, 2H). | 554.3 |
| 3 | 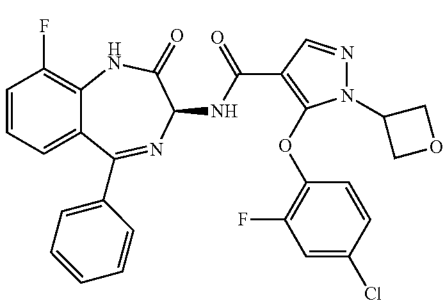 [SMILES: O=C(N[C@H]1N=C(c2ccccc2)c2cccc(F)c2NC1=O)c1cnn(C2COC2)c1Oc1ccc(Cl)cc1F] | 5-(4-Chloro-2-fluorophenoxy)-N-[(3S)-9-fluoro-2-oxo-5-phenyl-1,3-dihydro-1,4-benzodiazepin-3-yl]-1-(oxetan-3-yl)pyrazole-4-carboxamide | 10.82 (s, 1H), 9.20 (d, J = 7.9 Hz, 1H), 8.59 (s, 1H), 7.65-7.39 (m, 7H), 7.34-7.22 (m, 1H), 7.16-7.06 (m, 2H), 6.81 (t, J = 9.0 Hz, 1H), 5.62-5.47 (m, 1H), 5.34 (d, J = 7.9 Hz, 1H), 4.96-4.75 (m, 4H). | 564.2 |

| Example | Structure | Name | ¹H NMR δ (400 MHz, DMSO-d₆) | LRMS [M + H]⁺ |
|---|---|---|---|---|
| 4 | 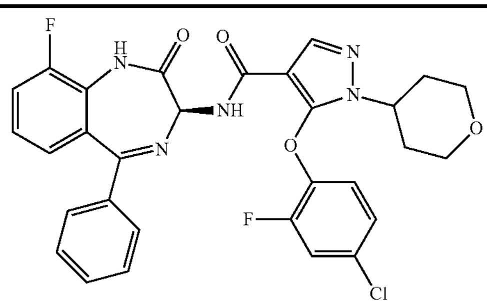 | 5-(4-Chloro-2-fluorophenoxy)-N-[(3S)-9-fluoro-2-oxo-5-phenyl-1,3-dihydro-1,4-benzodiazepin-3-yl]-1-(oxan-4-yl)pyrazole-4-carboxamide | 10.81 (s, 1H), 9.13 (d, J = 7.9 Hz, 1H), 8.47 (s, 1H), 7.61-7.40 (m, 7H), 7.35-7.21 (m, 1H), 7.18-7.06 (m, 2H), 6.80 (t, J = 9.0 Hz, 1H), 5.34 (d, J = 7.9 Hz, 1H), 4.50-4.35 (m, 1H), 3.98-3.83 (m, 2H), 3.50-3.40 (m, 2H), 2.15-1.94 (m, 2H), 1.86-1.66 (m, 2H). | 592.3 |
| 5 | 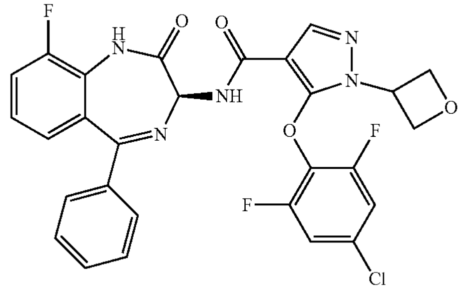 | 5-(4-Chloro-2,6-difluorophenoxy)-N-[(3S)-9-fluoro-2-oxo-5-phenyl-1,3-dihydro-1,4-benzodiazepin-3-yl]-1-(oxetan-3-yl)pyrazole-4-carboxamide | 10.82 (s, 1H), 9.23 (d, J = 8.1 Hz, 1H), 8.55 (s, 1H), 7.65-7.33 (m, 8H), 7.33-7.21 (m, 1H), 7.11 (d, J = 7.9 Hz, 1H), 5.87-5.73 (m, 1H), 5.31 (d, J = 8.0 Hz, 1H), 5.02-4.84 (m, 4H). | 582.2. |
| 6 | 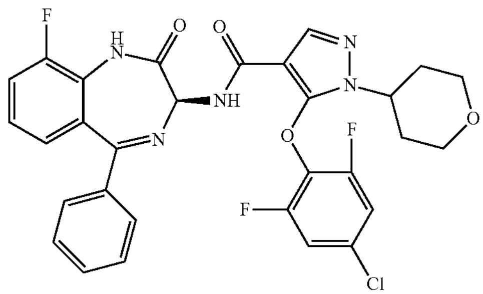 [SMILES: O=C(N[C@H]1N=C(c2ccccc2)c2cccc(F)c2NC1=O)c1cnn(C2CCOCC2)c1Oc1ccc(Cl)cc1F] | 5-(4-Chloro-2,6-difluorophenoxy)-N-[(3S)-9-fluoro-2-oxo-5-phenyl-1,3-dihydro-1,4-benzodiazepin-3-yl]-1-(oxan-4-yl)pyrazole-4-carboxamide | 10.82 (s, 1H), 9.14 (d, J = 8.1 Hz, 1H), 8.41 (s, 1H), 7.63-7.33 (m, 8H), 7.33-7.22 (m, 1H), 7.11 (d, J = 7.9 Hz, 1H), 5.30 (d, J = 8.1 Hz, 1H), 4.76-4.57 (m, 1H), 4.05-3.89 (m, 2H), 3.57-3.43 (m, 2H), 2.14-1.96 (m, 2H), 1.89-1.77 (m, 2H). | 610.3. |

Example 7: Efficacy In Vitro

Compounds were subjected to an RSV plaque reduction assay according to the following protocol.

Plaque Reduction Assay:

Hep-G2 cells (ECACC, 85011430) were passaged in flasks and seeded in 24-well plates in DMEM containing antibiotics and supplemented with 10% FBS. During inoculation and subsequent incubation, cells were cultured in DMEM containing 2% FBS. 100 plaque forming unit/well of RSV (RSV A2 ECACC, 0709161v) was mixed with eight serial dilutions of compound. Subsequently, 100 µL of the virus/compound mixtures was added to confluent Hep-G2 cell monolayers. The cells and virus/compound mixtures were incubated at 37° C. in a humidified 5% $CO_2$ incubator for 2 h prior to removal of the inoculum and addition of 1 mL of overlay (DMEM containing FBS and 0.8% CMC) containing compound dilutions. The cells and were incubated at 37° C. in a humidified 5% $CO_2$ incubator for 2 days.

Cells were washed with PBS before adding 75/25% v/v EtOH/MeOH, for 3 min. Fixative was removed and plates were washed with PBS. A pre-titrated amount of the primary antibody was added in 200 µL PBS/2% milk powder, and plates incubated for 90 min at 37° C. The plates were washed 3 times with PBS/0.05% Tween20 before addition of rabbit anti-goat horse radish peroxidase in 200 µL PBS/2% milk powder, and incubated for 1 h at 37° C. Following three wash steps with PBS/0.05% Tween20, 200 µL ready-to-use TrueBlue was added and plates were incubated at rt for 10-15 min before washing with water. After removal of water, plates were air-dried in the dark.

Plates were scanned and analysed using the Immunospot S6 Macro analyser, which is equipped with BioSpot analysis software for counting immunostained plaques (virospots). Plaque counts were used to calculate % infection relative to the mean of the plaque count in the virus control wells for RSV. The $EC_{50}$ value was calculated as 50% reduction in signal, respectively, by interpolation of inhibition curves fitted with a 4-parameter nonlinear regression with a variable slope in Dotmatics. Plaque $EC_{50}$ and cell toxicity $CC_{50}$ values are a mean of at least two experiments and figures are rounded to whole units.

Results

| Example | RSV A2 Plaque $EC_{50}$ (nM) | Cell Cytotoxicity $CC_{50}$ (nM) |
|---|---|---|
| 1 | 91 | >25,000 |
| 2 | 89 | >25,000 |

-continued

| Example | RSV A2 Plaque EC$_{50}$ (nM) | Cell Cytotoxicity CC$_{50}$ (nM) |
|---|---|---|
| 3 | 71 | >25,000 |
| 4 | 67 | >25,000 |
| 5 | 74 | >25,000 |
| 6 | 55 | >25,000 |

Example 7: In Vitro Pharmacokinetics

Compounds were subjected to the following assays to investigate liver microsomal stability.
Microsomal Incubation: Experimental Procedure Pooled liver microsomes were purchased from a reputable commercial supplier and stored at −80° C. prior to use. Microsomes (final protein concentration 0.5 mg/mL), 0.1 M phosphate buffer pH 7.4 and test compound (final substrate concentration 1 µM; final DMSO concentration 0.25%) were pre-incubated at 37° C. prior to the addition of NADPH (final concentration 1 mM) to initiate the reaction. The final incubation volume was 50 uL. A control incubation was included for each compound tested where 0.1 M phosphate buffer pH 7.4 was added instead of NADPH (minus NADPH). Two control compounds were included with each species. All incubations were performed singularly for each test compound. Each compound was incubated for 0, 5, 15, 30 and 45 min. The control (minus NADPH) was incubated for 45 min only. The reactions were stopped by transferring incubate into acetonitrile at the appropriate time points, in a 1:3 ratio. The termination plates are centrifuged at 3,000 rpm for 20 min at 4° C. to precipitate the protein. Following protein precipitation, the sample supernatants were combined in cassettes of up to 4 compounds, internal standard added, and samples analysed by LC-MS/MS. From a plot of ln peak area ratio (compound peak area/internal standard peak area) against time, the gradient of the line was determined. Subsequently, half-life ($t_{1/2}$) and intrinsic clearance ($CL_{int}$) were calculated.

Results

| Example | Liver Microsomal Stability t½ (min); rat/dog/human |
|---|---|
| 1 | 5.0/38.6/36.0 |
| 3 | 38.3/140/24.5 |
| 4 | 19.7/117/38.8 |
| 5 | 42.3/174/15.8 |

Example 8: Aqueous Formulation

The compound of Example 1 is formulated as a solution in 30% w/v captisol (i.e. sulfobutylether-beta-cyclodextrin) at pH4 according to the following procedure.

A carrier of 30% w/v captisol (i.e. sulfobutylether-beta-cyclodextrin) is prepared by weighing the required amount of captisol into a suitable vessel, adding approximately 80% of the final volume of water and magnetically stirring until a solution is formed. The carrier is then made up to volume with water.

An aqueous solution of a compound of Example 1 is prepared by weighing 175 mg of the compound into a suitable vessel and adding approximately 80% of the required volume of the carrier. Using an aqueous solution of hydrochloric acid, the pH is adjusted to pH2 and the resulting mixture is magnetically stirred until a solution is formed. The formulation is then made up to volume with carrier and the pH is adjusted to pH4 using an aqueous solution of sodium hydroxide.

Example 9: Tablet Composition

Tablets, each weighing 0.15 g and containing 25 mg of a compound of the invention are manufactured as follows:
Composition for 10,000 Tablets
  Compound of the invention (250 g)
  Lactose (800 g)
  Corn starch (415 g)
  Talc powder (30 g)
  Magnesium stearate (5 g)

The compound of the invention, lactose and half of the corn starch are mixed. The mixture is then forced through a sieve 0.5 mm mesh size. Corn starch (10 g) is suspended in warm water (90 mL). The resulting paste is used to granulate the powder.

We claim:

1. A compound which is a benzodiazepinyl pyrazole of formula (I):

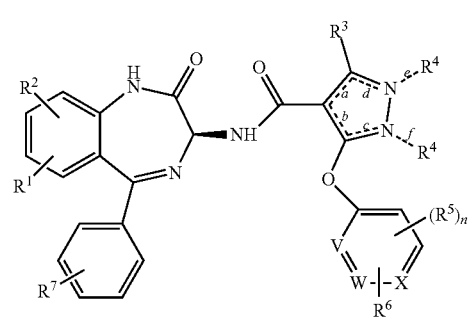

wherein:
each of $R^1$ and $R^2$ is independently H or halo;
$R^3$ is H, $C_1$-$C_6$ alkyl or —NHR$^8$;
either (i) ---a--, ---c-- and ---e-- are all bonds, with ---b--, ---d-- and ---f-- absent; or
---b--, ---d-- and ---f-- are all bonds, with ---a--, ---c-- and ---e-- absent;
$R^4$ is H or a group selected from $C_1$-$C_6$ alkyl, $C_3$-$C_6$ cycloalkyl and 4- to 10-membered heterocyclyl, the group being unsubstituted or substituted;
$R^5$ is H or halo;
$R^6$ is —OR$^8$, —NR$^8$R$^9$ or —R$^8$;
$R^7$ is H or halo;
each of $R^8$ and $R^9$ is independently H or a group selected from $C_1$-$C_6$ alkyl, $C_3$-$C_6$ cycloalkyl and 4- to 10-membered heterocyclyl, the group being unsubstituted or substituted;
n is 1 or 2; and
one of V, W and X is N or CH and the other two are CH;
or a pharmaceutically acceptable salt thereof.

2. A compound according to claim 1, wherein $R^2$ is a halo substituent at the 9-position of the benzodiazepinyl ring system.

3. A compound according to claim 1 wherein ---a---, ---c--- and ---e--- are all bonds, with ---b---, ---d--- and ---f--- absent.

4. A compound according to claim 1 wherein ---b---, ---d--- and ---f--- are all bonds, with ---a---, ---c--- and ---e--- absent.

5. A compound according to claim 1 wherein V and W are both CH and X is N or CH.

6. A compound according to claim 1 wherein $R^2$ is F at the 9-position of the benzodiazepinyl ring system.

7. A compound according to claim 1 wherein n is 1, $R^5$ is at ring position 2 and Re is at ring position 4 of the six-membered ring to which they are both bonded.

8. A compound according to claim 1 which is selected from:
- 5-(2,6-Difluoro-4-methylphenoxy)-1-ethyl-N-[(3S)-2-oxo-5-phenyl-1,3-dihydro-1,4-benzodiazepin-3-yl] pyrazole-4-carboxamide;
- 5-(2-Fluoro-4-methylphenoxy)-1-(oxan-4-yl)-N-[(3S)-2-oxo-5-phenyl-1,3-dihydro-1,4-benzodiazepin-3-yl] pyrazole-4-carboxamide;
- 5-(4-Chloro-2-fluorophenoxy)-N-[(3S)-9-fluoro-2-oxo-5-phenyl-1,3-dihydro-1,4-benzodiazepin-3-yl]-1-(oxetan-3-yl) pyrazole-4-carboxamide;
- 5-(4-Chloro-2-fluorophenoxy)-N-[(3S)-9-fluoro-2-oxo-5-phenyl-1,3-dihydro-1,4-benzodiazepin-3-yl]-1-(oxan-4-yl) pyrazole-4-carboxamide;
- 5-(4-Chloro-2,6-difluorophenoxy)-N-[(3S)-9-fluoro-2-oxo-5-phenyl-1,3-dihydro-1,4-benzodiazepin-3-yl]-1-(oxetan-3-yl) pyrazole-4-carboxamide;
- 5-(4-Chloro-2,6-difluorophenoxy)-N-[(3S)-9-fluoro-2-oxo-5-phenyl-1,3-dihydro-1,4-benzodiazepin-3-yl]-1-(oxan-4-yl) pyrazole-4-carboxamide;

and the pharmaceutically acceptable salts thereof.

9. A pharmaceutical composition which comprises a compound as defined in claim 1 and a pharmaceutically acceptable carrier or diluent.

10. A method for treating a subject suffering from or susceptible to an RSV infection, which method comprises administering to said subject an effective amount of a compound as defined in claim 1.

11. A pharmaceutical composition which comprises (a) a compound as defined in claim 1, and (b) one or more further therapeutic agents, together with a pharmaceutically acceptable carrier or diluent, wherein the further therapeutic agent is selected from the group consisting of:
(i) a RSV nucleocapsid (N)-protein inhibitor;
(ii) a protein inhibitor that inhibits the phosphoprotein (P) protein and/or large (L) protein;
(iii) an anti-RSV monoclonal antibody;
(iv) an immunomodulating toll-like receptor compound;
(v) a respiratory virus anti-viral; and
(vi) an anti-inflammatory compound.

12. A process for producing a pharmaceutically acceptable salt as defined in claim 1, which process comprises treating a benzodiazepine derivative of formula (I) as defined in claim 1 with a suitable acid in a suitable solvent.

13. A process according to claim 11, wherein the acid is selected from hydrochloric acid, hydrobromic acid, hydroiodic acid, sulphuric acid, nitric acid, phosphoric acid, methanesulfonic acid, benzenesulphonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid.

14. A method according to claim 10, which method further comprises administering to the subject a further therapeutic agent selected from the group consisting of:
(i) a RSV nucleocapsid (N)-protein inhibitor;
(ii) a protein inhibitor that inhibits the phosphoprotein (P) protein and/or large (L) protein;
(iii) an anti-RSV monoclonal antibody;
(iv) an immunomodulating toll-like receptor compound;
(v) a respiratory virus anti-viral; and
(vi) an anti-inflammatory compound;
wherein the compound as defined in claim 1 and the further therapeutic agent are administered simultaneously, separately or sequentially.

15. The pharmaceutical composition of claim 11 wherein the anti-RSV monoclonal antibody is an F-protein antibody and the respiratory virus anti-viral is an anti influenza or anti rhinovirus compound.

16. The method of claim 14 wherein the anti-RSV monoclonal antibody is an F-protein antibody and the respiratory virus anti-viral is an anti influenza or anti rhinovirus compound.

* * * * *